(12) United States Patent
Nii et al.

(10) Patent No.: US 8,551,552 B2
(45) Date of Patent: Oct. 8, 2013

(54) OIL OR FAT COMPOSITION

(75) Inventors: Takanori Nii, Sumida-ku (JP); Hiroshi Tone, Sumida-ku (JP); Yoichi Arai, Sumida-ku (JP); Yoji Kameo, Sumida-ku (JP)

(73) Assignee: Kao Corporation, Tokyo (JP)

( * ) Notice: Subject to any disclaimer, the term of this patent is extended or adjusted under 35 U.S.C. 154(b) by 151 days.

(21) Appl. No.: 12/960,872

(22) Filed: Dec. 6, 2010

(65) Prior Publication Data

US 2011/0177226 A1 Jul. 21, 2011

(30) Foreign Application Priority Data

Dec. 7, 2009 (JP) ................................. 2009-277223

(51) Int. Cl.
*A23D 9/007* (2006.01)
(52) U.S. Cl.
USPC ........................................... 426/601; 426/460
(58) Field of Classification Search
USPC ....................................................... 426/601
See application file for complete search history.

(56) References Cited

U.S. PATENT DOCUMENTS

| | | | | |
|---|---|---|---|---|
| 4,166,868 A | * | 9/1979 | Ando et al. | 426/441 |
| 4,748,161 A | * | 5/1988 | Kimura et al. | 514/182 |
| 2004/0047971 A1 | * | 3/2004 | Alander | 426/601 |

FOREIGN PATENT DOCUMENTS

| | | | |
|---|---|---|---|
| CN | 1568725 A | | 1/2005 |
| CN | 101530137 A | | 9/2009 |
| JP | 58116415 | * | 7/1983 |
| JP | 2001-224309 | | 8/2001 |
| JP | 2003-310183 | | 11/2003 |
| JP | 2006-257064 | * | 9/2006 |
| WO | WO 99/56558 | * | 11/1999 |

OTHER PUBLICATIONS

Goh, E. M. 1985. JAOCS 62(4)730.*
Itoh, T. 1973. JAOCS 50:122.*
Itoh, T. 1973. JAOCS 50:300.*
Kitahara et al., 1983. Fat Science Part A, p. 259.*
Masanari Fujita et al., "Plant sterol", Arteriosclerosis, vol. 13, No. 2, Jun. 1985, pp. 273-278 (with Unedited Computer Generated Translation).
Zhou Huiming, et al., "The Present Situation and Tentative Idea of Improving White Rice Quality", Cereal & Feed industry, vol. 4, Apr. 10, 1998, pp. 10-11, (with English Abstract).
S. Meguro, et al., "Original Communication Solubilization of phytosterols in diacylglycerol versus triacylglycerol improves the serum cholesterol-lowering effect", European Journal of Clinical Nutrition, vol. 55, Jun. 14, 2001, pp. 513-517.

* cited by examiner

*Primary Examiner* — Carolyn Paden
(74) *Attorney, Agent, or Firm* — Oblon, Spivak, McClelland, Maier & Neustadt, L.L.P.

(57) ABSTRACT

Provided is an oil or fat composition including the following components (A) and (B): (A) a tetracyclic triterpene alcohol selected from the group consisting of 24-methylene cycloartanol and cyclobranol; and (B) an oil or fat containing diacylglycerol at 5 weight % or more.

14 Claims, No Drawings

OIL OR FAT COMPOSITION

BACKGROUND OF THE INVENTION

1. Field of the Invention

This application is based upon and claims the benefit of the priority of Japanese patent application No. 2009-277223, filed on Dec. 7, 2009, the disclosure of which is incorporated herein in its entirety by reference thereto.

The present invention relates to an oil or fat composition to be used for food such as rice.

2. Background of the Invention

Sterol is a collective term for steroids each having a hydroxy group at 3-position, which are contained in plants and animals. Typical examples of animal sterols are cholesterols. Plant sterols are classified into 4-desmethylsterols having 28 or 29 carbon atoms, such as β-sitosterol, stigmasterol, and campesterol, and into tetracyclic triterpene alcohols having 30 or 31 carbon atoms, such as cycloartenol, 24-methylene cycloartanol, and cyclobranol. In those plant sterols, the 4-desmethylsterols are known to have a cholesterol-lowering action and the like (JP-A-2001-224309).

On the other hand, the tetracyclic triterpene alcohols are known to be contained in a rice bran oil and the like, and are known to have a cholesterol-lowering action and a lipid absorption-inhibiting action (Arteriosclerosis, Vol. 13, No. 2, June (1985), 273-278, and JP-A-2001-224309).

However, those tetracyclic triterpene alcohols have a drawback in that the tetracyclic triterpene alcohols precipitate as crystals at room temperature, and hence a large amount of the tetracyclic triterpene alcohols cannot be contained in an oil or fat in a dissolved state. Thus, there is known a technology that involves dissolving tetracyclic triterpene alcohols in an edible oil or fat by combined use of oryzanols and phytosterols (JP-A-2006-257064).

In order to efficiently obtain the physiological actions of those tetracyclic triterpene alcohols, the tetracyclic triterpene alcohols are preferably ingestible without any effort at the time of routine diets, rather than the tetracyclic triterpene alcohols are ingested in the form of a capsule, a tablet, or the like. For that purpose, it is efficient to contain the tetracyclic triterpene alcohols in foodstuffs that are ingested daily, and it is most preferred that the tetracyclic triterpene alcohols be contained in staple foods such as rice and bread. According to such requirements, there is known cooked rice obtained by boiling raw rice with corn oil having added thereto plant sterols (JP-A-2003-310183).

[Patent Document 1] JP-A-2001-224309
[Patent Document 2] JP-A-2006-257064
[Patent Document 3] JP-A-2003-310183
[Non-Patent Document 1] Arteriosclerosis, Vol. 13, No. 2, June (1985), 273-278

SUMMARY OF THE INVENTION

The present invention provides an oil or fat composition including the following components (A) and (B):

(A) a tetracyclic triterpene alcohol selected from the group consisting of 24-methylene cycloartanol and cyclobranol; and (B) an oil or fat containing diacylglycerol at 5 weight % or more.

The present invention also provides raw rice or cooked rice having added thereto the above-mentioned oil or fat composition.

DETAILED DESCRIPTION OF THE INVENTION

The inventors of the present invention studied a technology of dissolving 24-methylene cycloartanol and cyclobranol among plant sterols in an oil or fat and adding the resulting oil or fat to a cooked rice. However, those plant sterols have low solubility in triglycerides, and hence they are able to be contained in the oil or fat only at a low concentration. As a result, when an oil or fat composition containing plant sterols at a high content is added to raw rice, followed by boiling the raw rice, a rough feeling is sensed during the mastication of the cooked rice. On the other hand, when an oil or fat composition containing plant sterols dissolved in rapeseed oil at a low concentration is added to raw rice, followed by boiled or cooked, there was found a drawback in that an oily taste was apt to be easily sensed from the boiled or cooked rice, and hence the taste of the boiled or cooked rice was impaired.

Thus, the present invention is to provide a composition that can be used for foodstuff ingested daily, such as cooked rice, the composition containing tetracyclic triterpene alcohols having excellent physiological activities such as a cholesterol-lowering action in a stably dissolved state at a high concentration.

Thus, the inventors of the present invention have studied an oil or fat composition that efficiently exerts the physiological actions of tetracyclic triterpene alcohols. As a result, the inventors have found that, by blending the tetracyclic triterpene alcohols in an oil or fat containing diacylglycerol at 5 weight % or more, the tetracyclic triterpene alcohols can be dissolved in the oil or fat at a high concentration, and hence a stable oil or fat composition can be obtained. Further, the inventors have found that, when the oil or fat composition is used to prepare cooked rice, good softness and stickiness can be imparted to the cooked rice totally unexpectedly.

According to the present invention, it is possible to provide an oil or fat composition that contains tetracyclic triterpene alcohols having excellent physiological actions such as a cholesterol-lowering action at a high concentration and that can be stably dispersed therein. Further, the use of the oil or fat composition can result in providing cooked rice having moderate softness and good stickiness.

(A) tetracyclic triterpene alcohols to be used for the present invention refer to triterpene alcohols having 30 or 31 carbon atoms, selected from 24-methylene cycloartanol and cyclobranol. Those triterpene alcohols having 30 or 31 carbon atoms are clearly different from 4-desmethylsterols having 28 or 29 carbon atoms, such as β-sitosterol, stigmasterol, and campesterol. Further, the triterpene alcohols are also clearly different from γ-oryzanols, which are ferulic acid esters of various plant sterols. Those triterpene alcohols having 30 or 31 carbon atoms can be obtained by extraction from rice oil or from an oil or fat and a processed product of an oil or fat each containing triterpene alcohols, or hydrolysis of γ-oryzanols, or the like. ORYZATRITERPENOID-P (Oryza Oil & Fat Chemical Co., Ltd.) and the like are exemplified as commercially available compositions containing the triterpene alcohols having 30 or 31 carbon atoms. Those compositions may contain one of 24-methylene cycloartanol and cyclobranol, or may contain a mixture of the two compounds. Further, the oil or fat composition of the present invention may contain any of triterpene alcohols other than the component (A), such as cycloartenol.

From the viewpoint of a cholesterol-lowering action, the oil or fat composition of the present invention contains preferably 24-methylene cycloartanol and/or cyclobranol, more preferably 24-methylene cycloartanol, among (A) the tetracyclic triterpene alcohols.

(B) an oil or fat to be used for the present invention contains diacylglycerol at 5 weight % or more. When the content of the diacylglycerol in the oil or fat is 5 weight % or more, (A) the tetracyclic triterpene alcohols are dissolved in a sufficient amount in the oil or fat, and good softness and stickiness can be imparted to cooked rice obtained by adding the oil or fat composition of the present invention. The content of the diacylglycerol in (B) the oil or fat is preferably 5 weight % or more, more preferably 10 to 98 weight %, more preferably 20 to 98 weight %, more preferably to 98 weight %, particularly preferably 55 to 98 weight %. Components other than the diacylglycerol in (B) the oil or fat include triacylglycerol and monoacylglycerol. The content of the monoacylglycerol is preferably 2 weight % or less, more preferably 1.5 weight % or less.

The diacylglycerol in (B) the oil or fat preferably include saturated fatty acids or unsaturated fatty acids each having 8 to 22 carbon atoms in their constituent fatty acids. Further, the oil or fat composition of the present invention can be used in the same way as a general edible oil or fat, and hence diacylglycerol to be used include unsaturated fatty acids at preferably 55 weight % or more, more preferably 70 weight % or more, in their constituent fatty acids. In particular, preferred are unsaturated fatty acids including oleic acid at 20 to 65 weight % and linoleic acid at 15 to 65 weight %.

(B) the oil or fat containing diacylglycerol is obtained by (1) carrying out a transesterification reaction between an oil or fat and glycerin or by (2) carrying out an esterification reaction by using fatty acids and glycerin. Those reactions may be carried out by any one of a chemical reaction caused by a hydroxide of an alkali (alkaline earth) metal as a catalyst and a reaction caused by an enzyme. When high-purity diacylglycerol are produced industrially, the enzymatic reaction according to the method (2) is preferred, because the chemical reaction according to the method (1) is apt to induce degradation of oil or fat, such as coloring.

As a raw material of fatty acid, it is possible to use (1) a fatty acid obtained by subjecting an oil or fat to a steam decomposition at 250 to 260° C. and distilling the resulting decomposed product, (2) a partial hydrolysate obtained by subjecting an oil or fat to a steam decomposition at 200 to 240° C., or (3) a partial hydrolysate obtained by decomposing an oil or fat by an enzymatic method at 20 to 70° C. Note that in any one of the methods, water is added at 20 to 180 parts by weight with respect to 100 parts by weight of the oil or fat to carry out the decomposition reaction.

A fatty acid obtained as described above is used to carry out an esterification reaction under a dehydration condition in the presence of a 1,3-selective lipase. As a result, it is possible to obtain a diacylglycerol (containing triglycerides at less than 20 weight % and monoglycerides at less than 5 weight %) with high yield together with a high purity of 80 weight % or more and a less discolored pale color (showing a 10R+Y value of 20 or less by the Lovibond method).

Further, a raw material of (B) the oil or fat to be used for the present invention is not particularly limited as long as the material is a general edible oil or fat. Examples of the material include naturally occurring the oil or fat derived from animals or plants and processed oil or fat obtained by subjecting the naturally occurring oil or fat to transesterification, hydrogenation, fractionation, or the like. Preferably used are plant oils such as soybean oil, rapeseed oil, rice bran oil, corn oil, and palm oil and processed fats or oils thereof.

From the viewpoints of the stability of the component (A) and the taste of cooked rice obtained by using the oil or fat composition of the present invention, the oil or fat composition of the present invention contains the component (A) at preferably 1 to 30 parts by weight, more preferably 5 to 25 parts by weight, particularly preferably 10 to 20 parts by weight with respect to 100 parts by weight of the component (B).

Further, the content of the component (A) in the oil or fat composition is preferably 1 to 30 weight %, more preferably 5 to 25 weight %, more preferably 7 to 20 weight %, particularly preferably 10 to 20 weight %.

The oil or fat composition of the present invention can be obtained by dissolving or dispersing the component (A) in the component (B).

The oil or fat composition of the present invention preferably further contains (C) an emulsifier. The incorporation of the emulsifier enhances the dispersibility of the composition in water, and hence the composition can be attached uniformly to rice and cooked rice. As a result, higher effects can be obtained. The emulsifier is not particularly limited as long as the emulsifier has compatibility with an oil or fat. Examples of the emulsifier include: various proteins such as an egg protein, a soybean protein, a milk protein, proteins separated from those proteins, and (partially) decomposed products of those proteins; glycerin fatty acid esters, organic acid-monoacylglycerol esters, polyglycerin fatty acid esters, propylene glycol fatty acid esters, polyglycerin-condensed ricinoleic acid esters, sorbitan fatty acid esters, and sucrose fatty acid esters; and lecithins or enzyme-decomposed products thereof. Preferred is glycerin fatty acid esters, polyglycerin fatty acid esters, and propylene glycol fatty acid esters, and more preferred is polyglycerin fatty acid esters in terms of taste.

The content of (C) the emulsifier in the oil or fat composition is preferably 1 to 30 weight %, more preferably 5 to 25 weight %, particularly preferably 10 to 25 weight %.

The oil or fat composition of the present invention is preferably an emulsified-type oil or fat composition further containing (D) water.

The content of (C) the emulsifier in the emulsified-type oil or fat composition is preferably 0.1 to 5 weight %, more preferably 1 to 3 weight %. The content of water is preferably 80 to 99 weight %, more preferably 85 to 95 weight %.

The content of the component (A) in the emulsified-type oil or fat composition is preferably 0.1 to 2.0 weight %, more preferably 0.5 to 1.9 weight %, more preferably 0.8 to 1.5 weight %, from the viewpoints of the softness and stickiness of cooked rice.

In addition, the content of the component (B) is preferably 1 to 10 weight %, more preferably 3 to 9 weight %, particularly preferably 5 to 8 weight %, from the viewpoint of taste and texture such as an oily taste of cooked rice.

The oil or fat composition of the present invention preferably contains an antioxidant at 50 to 2000 ppm for the purpose of storage stability and taste and flavor stability as a general edible oil or fat. Exemplified as the antioxidant is one or more members selected from a natural antioxidant, tocopherol, ascorbyl palmitate, ascorbyl stearate, BHT, BHA, phospholipids, and the like. More preferred is one or more members selected from a natural antioxidant, tocopherol, ascorbyl palmitate, phospholipids, and the like.

In addition, the oil or fat composition of the present invention may further contain a thickener, a taste-imparting agent, a flavor, a coloring agent, and the like. In this case, used as the thickener is a thickening polysaccharide such as a xanthane gum, a gellan gum, a guar gum, a carrageenan, a pectin, a tragacanth gum, a gum arabic, a locust bean gum, or a tamarind gum, or any of starches. Examples of the taste-imparting agent include an edible salt, a sugar, an edible vinegar, and a seasoning agent, and the like. The content of the thickener is preferably 0.01 to 0.2 weight %, more preferably 0.1 to 0.15 weight %.

The oil or fat composition of the present invention is preferably used as an oil or fat composition for cooked rice.

When the oil or fat composition of the present invention is used as an oil or fat composition for cooked rice, a tetracyclic triterpene alcohol selected from cycloartenol, 24-methylene cycloartanol, and cyclobranol can be used as a component (A') in place of the component (A), that is, a tetracyclic triterpene alcohol selected from 24-methylene cycloartanol and cyclobranol.

The content of the component (A') in the oil or fat composition is preferably 1 to 30 weight %, more preferably 5 to 25 weight %, more preferably 7 to 20 weight %, particularly preferably 10 to 20 weight %.

The oil or fat composition contains the component (A') at preferably 2 to 50 parts by weight, more preferably 10 to 40 parts by weight, particularly preferably 15 to 35 parts by weight with respect to 100 parts by weight of the component (B).

In addition, the oil or fat composition preferably contains (C) an emulsifier, and is preferably an emulsified-type oil or fat composition further containing (D) water.

When the oil or fat composition of the present invention is used as an oil or fat composition for cooked rice, for example, there is exemplified an embodiment in which the oil or fat composition is previously applied to raw rice. The application to raw rice can be made by using usual means such as coating or spraying. When raw rice to which the oil or fat composition of the present invention is applied, is boiled, the boiling may be performed in accordance with a usual method. However, in order to prevent the oil or fat composition from flowing out during the washing of the raw rice, the oil or fat composition is preferably applied to wash-free rice.

Further, in order for the oil or fat composition to be uniformly dispersed at the time of rice boiling, an oil or fat composition containing (C) the emulsifier described above is preferred.

Further, when the oil or fat composition of the present invention is used as an oil or fat composition for cooked rice, it is also possible to adopt an embodiment in which the oil or fat composition is added after the amount of water is adjusted at the time of rice boiling. This embodiment may be applied not only to wash-free rice but also to usual polished rice. In this case, in order for the oil or fat composition to be uniformly dispersed at the time of rice boiling, an oil or fat composition containing (C) the emulsifier described above is preferred, and further, an oil or fat composition in the form of an emulsified-type oil or fat composition further containing (D) water is more preferred from the viewpoint that the dispersibility of the oil or fat is exerted more favorably.

In order to produce cooked rice by using the oil or fat composition of the present invention, the oil or fat composition of the present invention may be added, for example, at preferably 1 to 20 parts by weight, more preferably 5 to 15 parts by weight with respect to 100 parts by weight of raw rice, followed by rice boiling in accordance with a usual method.

A water addition ratio at the time of rice boiling is more preferably 1.3 to 1.8 times by weight, more preferably 1.4 to 1.6 times by weight. In this case, the raw rice includes wash-free rice. Further, it is also possible that wash-free rice is previously subjected to surface treatment with the oil or fat composition of the present invention and the wash-free rice is boiled in accordance with a usual manner at the time of rice boiling. Note that the water addition ratio in this case is a ratio of the total amount of the oil or fat composition of the present invention and water with respect to the weight of raw rice.

The cooked rice obtained by using the oil or fat composition of the present invention contains the component (A), in terms of raw rice, at preferably 0.01 to 0.5 weight %, more preferably 0.02 to 0.3 weight %, particularly preferably 0.05 to 0.2 weight %.

Further, when the cooked rice obtained by using the oil or fat composition of the present invention is eaten, a rough feeling is not sensed and its improved taste is sensed. In addition, the cooked rice is good in softness and stickiness, which serve as indicators of taste, and hence its taste is good.

Further, there are provided a cholesterol-lowering action, an action of inhibiting an increase in a postprandial blood glucose level, an action of inhibiting an increase in a postprandial GIP level, and the like owing to the tetracyclic triterpene alcohols, and an action of promoting to burn body fat caused by diacylglycerol is expected.

EXAMPLE

The present invention is described in more detail by way of examples.

(Tetracyclic Triterpene Alcohol-Containing Preparation)

Used was ORYZA TRITERPENOID-P (Oryza Oil & Fat Chemical Co., Ltd.), which contains 24-methylene cycloartanol at 42 weight %, cyclobranol at 5 weight %, campesterol at 14 weight %, and cycloartenol at 39 weight %.

(Method of Preparing Diacylglycerol)

An esterification reaction was carried out in the presence of a 1,3-selective lipase by using glycerin and fatty acids (the composition of fatty acid: 4.1% palmitic acid, 1.9% stearic acid, 61.2% oleic acid, 19.3% linoleic acid, and 10.0% linolenic acid) obtained by decomposing rapeseed oil, to thereby synthesize diacylglycerol. Further, free fatty acids were removed by a distillation operation, and then steam deodorization under reduced pressure was carried out at 245° C. for 30 minutes at a pressure of 260 Pa at 3 wt % steam with respect to oil/hour, to thereby prepare a deodorized oil containing diacylglycerol as its main components. The composition of the deodorized oil was 0.1% free fatty acids, 1.2% monoacylglycerol, 83.7% diacylglycerol, and 15.0% triacylglycerol. In the deodorized oil, the content of unsaturated fatty acids was 94.5%, the content of oleic acid was 37.3%, and the content of linoleic acid was 48.0%.

(Method of Evaluating Taste of Boiled Rice)

Boiled rice was stirred in a rice kettle immediately after rice boiling, and then the boiled rice was transferred onto small plates to carry out the evaluation of taste.

(Criteria of Evaluation)

Stickiness
Score 5: Sticky
Score 4: Slightly sticky
Score 3: Slightly less sticky
Score 2: Less sticky
Score 1: Much less sticky Rough Feeling
Score 5: A rough feeling is not sensed.
Score 4: A rough feeling is hardly sensed.
Score 3: A rough feeling is sensed.
Score 2: A rough feeling is strongly sensed.
Score 1: A rough feeling is sensed very strongly.

Oily Taste
Score 5: An oily taste is not sensed.
Score 4: An oily taste is hardly sensed.
Score 3: An oily taste is sensed.
Score 2: An oily taste is strongly sensed.
Score 1: An oily taste is sensed very strongly.

Softness/Hardness
Score 5: Good softness
Score 4: Slightly good softness
Score 3: Slightly less soft
Score 2: Slightly hard
Score 1: Hard
Foreign Taste
Score 5: A foreign taste is not sensed.
Score 4: A foreign taste is hardly sensed.
Score 3: A foreign taste is slightly sensed.
Score 2: A foreign taste is sensed.
Score 1: A foreign taste is sensed very strongly.

Example 1

(Preparation of Oil or Fat Composition)
An emulsifier (Sunsoft A-181E: Taiyo Kagaku Co., Ltd., polyglycerin stearic acid ester) was weighed and 2.8 g of the emulsifier were put into a 150 ml glass container. Further, 1.5 g of ORYZA TRITERPENOID-P and 9.4 g of rapeseed oil containing 10% diacylglycerol as an oil or fat were added, and the whole was dissolved using a 95° C. hot water bath. After that, 90 g of water at 95° C. were added into the solution. An ultra disperser (Model LK-22, Yamato Scientific Co., Ltd.) was used to perform dispersion at 95° C. at 9000 rounds per minute for 1 minute, followed by further dispersion at 12,000 rounds per minute for 10 minutes. The whole was kept at 95° C. for 1 hour, and was then cooled to 30° C. at a rate of 1° C. per minute, to thereby produce an emulsified-type oil or fat composition.
(Method of Boiling Rice)
150 g of rice (Koshihikari harvested in Uonuma; Pearl Rice) were fed into a kettle of a rice cooker (Model RC-5JX, Toshiba Corporation) and were washed six times in ion-exchanged water. Then, 222.6 g of ion-exchanged water and 22.5 g of the emulsified-type oil or fat composition (water addition ratio: 1.5) were added and weighed. After that, immersion was performed at 25° C. for 30 minutes. After the immersion, the rice cooker was set up to boil rice. The boiled rice was stirred in the kettle immediately after the rice boiling, and then the boiled rice was transferred onto small plates to carry out the evaluation of taste.

Example 2

An oil or fat composition was prepared in the same manner as that in Example 1, except that an oil or fat having a diacylglycerol concentration of 84% was used in Example 1. The oil or fat composition was added, followed by rice boiling, and then the evaluation of taste was carried out.

Example 3

An oil or fat composition was prepared in the same manner as that in Example 1, except that 2.2 g of ORYZA TRITERPENOID-P and 8.7 g of rapeseed oil containing diacylglycerol at 25% were used to prepare the oil or fat composition in Example 1. The oil or fat composition was added, followed by rice boiling, and then the evaluation of taste was carried out.

Example 4

An oil or fat composition was prepared in the same manner as that in Example 3, except that an oil or fat having a diacylglycerol concentration of 84% was used in Example 3. The oil or fat composition was added, followed by rice boiling, and then the evaluation of taste was carried out.

Comparative Example 1

An oil or fat composition was prepared in the same manner as that in Example 3, except that rapeseed oil was used as an oil or fat in Example 3. The oil or fat composition was added, followed by rice boiling, and then the evaluation of taste was carried out.

Example 5

An oil or fat composition was prepared in the same manner as that in Example 1, except that 3.3 g of ORYZA TRITERPENOID-P and 7.7 g of rapeseed oil containing diacylglycerol at 10% were added to prepare the oil or fat composition, and moreover, 2.4 g of an emulsifying liquid were added at the time of rice boiling in Example 1. The oil or fat composition was added, followed by rice boiling, and then the evaluation of taste was carried out.

Example 6

An oil or fat composition was prepared in the same manner as that in Example 5, except that an oil or fat having a diacylglycerol concentration of 84% was used in Example 5. The oil or fat composition was added, followed by rice boiling, and then the evaluation of taste was carried out.

Comparative Example 2

An oil or fat composition was prepared in the same manner as that in Example 5, except that rapeseed oil was used as an oil or fat in Example 5. The oil or fat composition was added, followed by rice boiling, and then the evaluation of taste was carried out.

Example 7

An oil or fat composition was prepared in the same manner as that in Example 1, except that 3.3 g of ORYZA TRITERPENOID-P and 7.7 g of rapeseed oil containing diacylglycerol at 10% were added to prepare the oil or fat composition, and moreover, 30.0 g of an emulsifying liquid were added at the time of rice boiling in Example 1. The oil or fat composition was added, followed by rice boiling, and then the evaluation of taste was carried out.

Example 8

An oil or fat composition was prepared in the same manner as that in Example 7, except that an oil or fat having a diacylglycerol concentration of 84% was used in Example 7. The oil or fat composition was added, followed by rice boiling, and then the evaluation of taste was carried out.

Comparative Example 3

An oil or fat composition was prepared in the same manner as that in Example 7, except that rapeseed oil was used as an oil or fat in Example 7. The oil or fat composition was added, followed by rice boiling, and then the evaluation of taste was carried out.

The results obtained are shown in Table 1.

TABLE 1

| | | | Example 1 | Example 2 | Comparative Example 1 | Example 3 | Example 4 | Comparative Example 2 |
|---|---|---|---|---|---|---|---|---|
| Blending amount | Triterpene alcohol-containing preparation (*1) | [g] | 1.5 | 1.5 | 2.2 | 2.2 | 2.2 | 3.3 |
| | (A) Triterpene alcohol (*2) | [g] | 0.7 | 0.7 | 1.0 | 1.0 | 1.0 | 1.6 |
| | (B) Oil or fat | [g] | 9.4 | 9.4 | 8.7 | 8.7 | 8.7 | 7.7 |
| | (C) Emulsifier (*3) | [g] | 2.8 | 2.8 | 2.8 | 2.8 | 2.8 | 2.8 |
| | Water | [g] | 90.0 | 90.0 | 90.0 | 90.0 | 90.0 | 90.0 |
| | Total | [g] | 103.7 | 103.7 | 103.7 | 103.7 | 103.7 | 103.8 |
| Blending ratio | Triterpene alcohol-containing preparation (*1) | [%] | 1.4 | 1.4 | 2.1 | 2.1 | 2.1 | 3.2 |
| | (B) Oil or fat | [%] | 9.1 | 9.1 | 8.4 | 8.4 | 8.4 | 7.4 |
| | (C) Emulsifier (*3) | [%] | 2.7 | 2.7 | 2.7 | 2.7 | 2.7 | 2.7 |
| | (D) Water | [%] | 86.8 | 86.8 | 86.8 | 86.8 | 86.8 | 86.7 |
| | Total | [%] | 100.0 | 100.0 | 100.0 | 100.0 | 100.0 | 100.0 |
| | (A) Triterpene alcohol (*2) | [%] | 0.7 | 0.7 | 1.0 | 1.0 | 1.0 | 1.5 |
| | DAG content in oil or fat | [%] | 10 | 84 | 0 | 25 | 84 | 0 |
| | (A)/(B) | [—] | 0.08 | 0.08 | 0.12 | 0.12 | 0.12 | 0.20 |
| Rice boiling process | Raw rice | [g] | 150 | 150 | 150 | 150 | 150 | 150 |
| | Addition amount of emulsified-type oil or fat composition | [g] | 22.5 | 22.5 | 22.5 | 22.5 | 22.5 | 2.4 |
| | Content of component (A) in emulsified-type oil or fat composition | [g] [%] | 0.153 0.7 | 0.153 0.7 | 0.224 1.0 | 0.224 1.0 | 0.224 1.0 | 0.036 1.5 |
| | Content of component (B) in emulsified-type oil or fat composition | [g] [%] | 2.04 0.9 | 2.04 7.6 | 1.89 0.0 | 1.89 2.1 | 1.89 7.0 | 0.18 0.0 |
| Evaluation of taste of boiled rice | Stickiness | | 4 | 4 | 3 | 4 | 5 | 4 |
| | Rough feeling | | 5 | 5 | 3 | 5 | 5 | 3 |
| | Softness/hardness | | 5 | 5 | 3 | 4 | 5 | 3 |
| | Foreign taste | | 4 | 4 | 3 | 4 | 4 | 4 |

| | | | Example 5 | Example 6 | Comparative Example 3 | Example 7 | Example 8 |
|---|---|---|---|---|---|---|---|
| Blending amount | Triterpene alcohol-containing preparation (*1) | [g] | 3.3 | 3.3 | 3.3 | 3.3 | 3.3 |
| | (A) Triterpene alcohol (*2) | [g] | 1.6 | 1.6 | 1.6 | 1.6 | 1.6 |
| | (B) Oil or fat | [g] | 7.7 | 7.7 | 7.7 | 7.7 | 7.7 |
| | (C) Emulsifier (*3) | [g] | 2.8 | 2.8 | 2.8 | 2.8 | 2.8 |
| | Water | [g] | 90.0 | 90.0 | 90.0 | 90.0 | 90.0 |
| | Total | [g] | 103.8 | 103.8 | 103.8 | 103.8 | 103.8 |
| Blending ratio | Triterpene alcohol-containing preparation (*1) | [%] | 3.2 | 3.2 | 3.2 | 3.2 | 3.2 |
| | (B) Oil or fat | [%] | 7.4 | 7.4 | 7.4 | 7.4 | 7.4 |
| | (C) Emulsifier (*3) | [%] | 2.7 | 2.7 | 2.7 | 2.7 | 2.7 |
| | (D) Water | [%] | 86.7 | 86.7 | 86.7 | 86.7 | 86.7 |
| | Total | [%] | 100.0 | 100.0 | 100.0 | 100.0 | 100.0 |
| | (A) Triterpene alcohol (*2) | [%] | 1.5 | 1.5 | 1.5 | 1.5 | 1.5 |
| | DAG content in oil or fat | [%] | 10 | 84 | 0 | 10 | 84 |
| | (A)/(B) | [—] | 0.20 | 0.20 | 0.20 | 0.20 | 0.20 |
| Rice boiling process | Raw rice | [g] | 150 | 150 | 150 | 150 | 150 |
| | Addition amount of emulsified-type oil or fat composition | [g] | 2.4 | 2.4 | 30.0 | 30.0 | 30.0 |
| | Content of component (A) in emulsified-type oil or fat composition | [g] [%] | 0.036 1.5 | 0.036 1.5 | 0.448 1.5 | 0.448 1.5 | 0.448 1.5 |
| | Content of component (B) in emulsified-type oil or fat composition | [g] [%] | 0.18 0.7 | 0.18 6.2 | 2.23 0.0 | 2.23 0.7 | 2.23 6.2 |
| Evaluation of taste of boiled rice | Stickiness | | 5 | 5 | 3 | 4 | 5 |
| | Rough feeling | | 5 | 5 | 3 | 5 | 5 |
| | Softness/hardness | | 4 | 5 | 4 | 5 | 5 |
| | Foreign taste | | 4 | 4 | 3 | 4 | 4 |

(*1) ORYZA TRITERPENOID-P (Oryza Oil & Fat Chemical Co., Ltd.)
(*2) 24-methylene cycloartanol and cyclobranol
(*3) SunSoft A-181E: Taiyo Kagaku Co., Ltd.

As is evident from Table 1, the cooked rice obtained by boiling raw rice with addition of the oil or fat composition including (A) tetracyclic triterpene alcohols and (B) an oil or fat containing diacylglycerol is good in taste and has good softness.

What is claimed is:

1. An oil or fat composition comprising the following components (A) and (B):
    (A) a tetracyclic triterpene alcohol selected from the group consisting of 24-methylene cycloartanol and cyclobranol; and
    (B) an oil or fat containing diacylglycerol at 10 to 98 weight %,
    wherein the component (A) is contained at 1 to 30 parts by weight with respect to 100 parts by weight of the component (B).

2. The oil or fat composition according to claim 1, wherein the oil or fat composition comprises an edible oil or fat composition.

3. The oil or fat composition according to claim 1, further comprising (C) an emulsifier and (D) water, wherein the oil or fat composition comprises an emulsified-type oil or fat composition.

4. The oil or fat composition according to claim 2, further comprising (C) an emulsifier and (D) water, wherein the oil or fat composition comprises an emulsified-type oil or fat composition.

5. An oil or fat composition, comprising the following components (A') and (B):
    (A') a tetracyclic triterpene alcohol selected from the group consisting of cycloartenol, 24-methylene cycloartanol and cyclobranol; and
    (B) an oil or fat containing diacylglycerol at 10 to 98 weight %,
    wherein the component (A') is contained at 2 to 50 parts by weight with respect to 100 parts by weight of the component (B);
    and wherein said oil or fat composition is in a form suitable for cooked rice.

6. The oil or fat composition according to claim 5, further comprising (C) an emulsifier and (D) water, wherein the oil or fat composition comprises an emulsified-type oil or fat composition.

7. A raw rice having added thereto the oil or fat composition according to claim 6.

8. A cooked rice having added thereto the oil or fat composition according to claim 6.

9. A method of producing a cooked rice, comprising: adding the oil or fat composition according to claim 6 to a raw rice; and boiling the raw rice.

10. A method of producing a cooked rice, comprising: adding the oil or fat composition according to claim 6 at 1 to 20 parts by weight with respect to 100 parts by weight of the raw rice; and boiling the raw rice.

11. A raw rice having added thereto the oil or fat composition according to claim 5.

12. A cooked rice having added thereto the oil or fat composition according to claim 5.

13. A method of producing a cooked rice, comprising: adding the oil or fat composition according to claim 5 to a raw rice; and boiling the raw rice.

14. A method of producing a cooked rice, comprising: adding the oil or fat composition according to claim 5 at 1 to 20 parts by weight with respect to 100 parts by weight of the raw rice; and boiling the raw rice.

* * * * *